(12) United States Patent
Xia et al.

(10) Patent No.: US 10,071,165 B2
(45) Date of Patent: Sep. 11, 2018

(54) PROTEIN-CELL CONJUGATE, PREPARATION METHOD AND USE THEREOF

(71) Applicant: CANSBIO (BEIJING) BIOTECHNOLOGY CO., LTD., BDA, Beijing (CN)

(72) Inventors: Changqing Xia, Beijing (CN); Yixian Guo, Weifang (CN); Haitao Wu, Beijing (CN); Suigui Wan, Weifang (CN)

(73) Assignee: CANSBIO (BEIJING) BIOTECHNOLOGY CO., LTD., Beijing (CN)

(*) Notice: Subject to any disclaimer, the term of this patent is extended or adjusted under 35 U.S.C. 154(b) by 0 days.

(21) Appl. No.: 14/898,209

(22) PCT Filed: May 29, 2014

(86) PCT No.: PCT/CN2014/078817
§ 371 (c)(1),
(2) Date: Feb. 9, 2016

(87) PCT Pub. No.: WO2014/198184
PCT Pub. Date: Dec. 18, 2014

(65) Prior Publication Data
US 2016/0228561 A1 Aug. 11, 2016

(30) Foreign Application Priority Data

Jun. 14, 2013 (CN) .......................... 2013 1 0234603

(51) Int. Cl.
*A61K 39/385* (2006.01)
*A61K 39/00* (2006.01)
(Continued)

(52) U.S. Cl.
CPC .......... *A61K 47/4833* (2013.01); *A61K 35/17* (2013.01); *A61K 38/18* (2013.01);
(Continued)

(58) Field of Classification Search
CPC ...... A61K 35/17; A61K 39/385; A61K 38/18; A61K 38/22; A61K 39/0011;
(Continued)

(56) References Cited

U.S. PATENT DOCUMENTS 5,328,840 A 7/1994 Coller
2008/0254058 A1 10/2008 Glenting et al.

FOREIGN PATENT DOCUMENTS

| CN | 1628844 A | 6/2005 |
| CN | 101120088 A | 2/2008 |
| WO | 2010141566 A1 | 12/2010 |
| WO | 2012135522 A2 | 10/2012 |

OTHER PUBLICATIONS

Cooper et al. Serum B-microglobulin and C reactive protein concentrations in viral infections J. Clin. Pathol. 1984, vol. 37, pp. 1140-1143.*
(Continued)

*Primary Examiner* — Shafiqul Haq
(74) *Attorney, Agent, or Firm* — Novick, Kim & Lee, PLLC; Allen Xue

(57) ABSTRACT

The present invention pertains to immunology, biomedicine field, specifically relates to a protein-cell conjugate, which is characterized in that the protein and the cell are coupled via a bifunctional cross-linking agent. The present invention further relates to a preparation method and uses of the protein-cell conjugate. The protein-cell conjugate of the present invention can be used for prevention or treatment of many diseases, such as malignant tumors, infectious diseases and autoimmune diseases.

2 Claims, 8 Drawing Sheets

(51) Int. Cl.
| | |
|---|---|
| A61K 47/48 | (2006.01) |
| A61K 38/18 | (2006.01) |
| A61K 38/22 | (2006.01) |
| A61K 35/17 | (2015.01) |
| A61K 47/62 | (2017.01) |
| A61K 47/69 | (2017.01) |

(52) U.S. Cl.
CPC .......... *A61K 38/22* (2013.01); *A61K 39/0011* (2013.01); *A61K 39/385* (2013.01); *A61K 47/62* (2017.08); *A61K 47/6901* (2017.08); A61K 2039/5156 (2013.01); A61K 2039/54 (2013.01); A61K 2039/55566 (2013.01); A61K 2039/575 (2013.01); A61K 2039/6006 (2013.01); A61K 2039/62 (2013.01); A61K 2039/627 (2013.01)

(58) Field of Classification Search
CPC ................ A61K 47/4833; A61K 47/62; A61K 47/6901; A61K 2039/6006; A61K 2039/627; A61K 2039/55566; A61K 2039/5156; A61K 2039/54; A61K 2039/62; A61K 2039/575
See application file for complete search history.

(56) References Cited

OTHER PUBLICATIONS

Shiu et al. Expression of bets-2-microglobulin by nasopharyngeal carcinoma. Br. J. Cancer. 1992, vol. 66, pp. 555-557.*

Mamula et al. The specificity of human anti-cytochrome c autoantibodies that arise in autoimmune disease. J. Immunol. 1990, vol. 144, No. 5, pp. 1835-1840.*

Fandes et al. The proteoglycan repertoire of lymphoid cells. Glycoconj. J. 2012, vol. 29, pp. 513-523. (Year: 2013).*

Park et al. Cell surface heparan sulfate proteoglycans: selective regulators of ligand-receptor encounters. J.B.C. 2000, vol. 275, No. 39, pp. 29923-29926 (Year: 2000).*

Sung et al. Glypican-3 is overexpressed in human hepatocellular carcinoma. Cancer Sci 2003, vol. 94, No. 3, pp. 259-262. (Year: 2003).*

Christiaansen et al., "Rapid Covalent Coupling of Proteins to Cell Surfaces; Immunological Characterization of Viable Protein-Cell Conjugates," Journal of Immunological Methods, 1984, vol. 74, pp. 229-239.

Sahaf et al., "Lymphocyte surface thiol levels," PNAS, Apr. 1, 2003, vol. 100, No. 7, pp. 4001-4005.

1991—"Functional expression of the CD4 protein after cross-linking to red blood cells with bifunctional reagent"—Idziorek, et. al.—Biochimica et Biophysica Acta.

Sep. 30, 2010—"Therapeutic cell engineering with surface-conjugated synthetic nanoparticles"—Stephan, M.T. et al—Nature Medicine.

Sep. 4, 2014—ISR and WO—App PCT/CN2014/078817—Eng Tran.

Sep. 30, 2000—"Therapeutic cell engineering with surface-conjugated synthetic nanoparticles"—Stephan, M.T. et al—Nature Medicine.

Notification of Reasons for Rejection for JP 2016518825, dated Oct. 3, 2017, 12 pages.

* cited by examiner

A

B

PROTEIN-CELL CONJUGATE, PREPARATION METHOD AND USE THEREOF

CROSS-REFERENCE TO RELATED APPLICATIONS

This application is a U.S. National Stage application under 35 U.S.C. § 371 of International Application PCT/CN2014/078817 (published as WO 2014/198184 A1), filed May 29, 2014, which claims priority to Application CN 201310234603.3, filed Jun. 14, 2013. Benefit of the filing date of each of these prior applications is hereby claimed. Each of these prior applications is hereby incorporated by reference in its entirety.

TECHNICAL FIELD

The present invention pertains to immunology and biomedicine field, and relates to a conjugate, especially a conjugate of a protein and a cell. The present invention further relates to a preparation method and use of the protein-cell conjugate.

BACKGROUND ART

The occurrence and development of tumor relate to hypofunction of immune surveillance, some infections could be effectively prevented by administration of vaccines against pathogenic microorganism, and immune tolerance could be restored by immune regulation or induction of immune tolerance in autoimmune diseases caused by autoimmune tolerance impairment. All these immunologic intervention means relate to antigens or antibodies, while most of antigens or antibodies are proteins. Hence, the above immunologic intervention means primarily aim at inducing immunoreaction against or immune tolerance to antigen proteins or taking full advantage of targeting ability of antibodies.

The key to achieve the aforesaid immunologic intervention is how to efficiently convey antigen protein to lymphatic tissue. If an antigen protein is effectively and firmly coupled to the surface of an immune cell, the antigen protein could be efficiently conveyed to lymphatic tissue or presented better via infusion of the immune cell because the immune cell has feature of immigrating to and positioning at lymphatic tissue or feature of presenting an antigen. Alternatively, immune effector cells could be anchored at target cells by using targeting ability of antibody, so as to improve killing efficiency of the immune effector cells.

One of known methods of coupling a protein to cell membrane comprises coupling a known antigen to cell surface by cell fixation with ethylene carbodiimide (ECDI) (luo, et al. Proc Natl AcadSci USA. 2008 Sep. 23; 105 (38):14527-32.; Smarr C B, et al. Antigen-fixed leukocytes tolerize Th2 responses in mouse models of allergy. J Immunol. 2011 Nov. 15; 187 (10):5090-8.). The cells prepared by this method are dead due to ECDI fixation, and according to this article, the infusion of these cells could only induce antigen specific immunologic tolerance, but could not induce immunologic response to the antigen.

Hence, it is still in need in the art to provide a method of coupling a protein to a living cell, so as to induce more efficiently the immunologic response useful in prophylaxis or treatment of infection and tumors.

Contents of the Invention

After long-term and a large amount of experimental researches, the inventors of the present invention surprisingly found that a protein could be coupled to a cell by using a bifunctional cross-linking agent, wherein the activities of the protein and the cell are maintained, thereby fulfilling the present invention.

The first aspect of the present invention relates to a protein-cell conjugate, which is a conjugate formed by covalently linking a protein and a cell to a linker, respectively; preferably, the cell has free sulfhydryl groups distributed on its surface, when the cell is not linked to the linker; preferably, the linker is derived from a bifunctional cross-linking agent, and the bifunctional cross-linking agent comprises both a group capable of reacting with an amino group and a group capable of reacting with a sulfhydryl group.

According to the protein-cell conjugate of any item of the first aspect of the present invention, wherein the cell is a cell with immunologic function; preferably, the cell is at least one selected from the group consisting of lymphocytes, monocytes, macrophages, dendritic cells, and natural killer cells.

In some embodiments of the present invention, the cell is lymphocyte, and for example, the lymphocyte is T lymphocyte or B lymphocyte.

According to the protein-cell conjugate of any item of the first aspect of the present invention, wherein the linker is derived from a bifunctional cross-linking agent.

In some specific embodiments of the present invention, the bifunctional cross-linking agent comprises both a succinimidyl group and a maleimidyl group.

In some embodiments of the present invention, any compounds comprising both succinimidyl group and maleimidyl group can fulfill the present invention. In some specific embodiments of the present invention, the compounds include but are not limited to succinimidyl4-(N-maleimidomethyl)-cyclohexane-1-carboxylate (SMCC) or analogues thereof, N-succinimidyl-4-(N-maleimidomethyl)-cyclohexane-1-carboxy-(6-aminocaproate), which is a long-chain analogue of SMCC (LC-SMCC), (N-maleimidomethyl)-cyclohexane-1-carboxylic acid-3-sulfosuccinimide ester (SULFO-SMCC), κ-maleimido-undecanoic acid N-succinimidyl ester (KMUA), γ-maleimidobutyric acid N-succinimidyl ester (GMBS), ε-maleimidocaproic acid N-hydroxysuccinimidyl ester (EMCS), meta-maleimidobenzoyl-N-hydroxysuccinimide ester (MBS), N-(α-maleimidoacetoxy)-succinimide ester (AMAS), succinimidyl-6-(β-maleimidopropionylamino) hexanoate (SMPH) or N-succinimidyl 4-(para-maleimidophenyl)-butyrate (SMPB).

According to the protein-cell conjugate of any item of the first aspect of the present invention, the succinimidyl of the bifunctional cross-linking agent reacts with a free amino group of the protein to form an amido linkage, and the maleimidyl of the bifunctional cross-linking agent reacts with the free sulfhydryl group on the cell to form a thioether linkage.

According to the protein-cell conjugate of any item of the first aspect of the present invention, the protein includes but is not limited to antigen proteins (e.g., tumor associated antigens, antigens associated with infectious diseases, antigens associated with autoimmune diseases), epitopes, antibodies, hormones, growth factors, vitamins, colony stimulating factors.

In an embodiment of the present invention, the protein is keyhole limpet hemocyanin (KLH); in another embodiment, the protein is insulin. In another embodiment, the protein is liver cancer associated protein, glypican-3 (GPC3).

The second aspect of the present invention relates to a method for preparing a protein-cell conjugate, which comprises the following steps:

(1) contacting a protein with a bifunctional cross-linking agent so that a linking group of the bifunctional cross-linking agent covalently links to the protein, thereby obtaining a first mixture, which comprises the protein linked to the linking group;

(2) optionally, further comprising a step of removing the unlinked bifunctional cross-linking agent from the first mixture, to obtain a purified protein linked to the linking group;

(3) contacting the protein linked to the linking group obtained in step (1) or (2) with a cell, so that another linking group covalently links to the cell, thereby obtaining a second mixture, which comprises a conjugate of the protein and the cell which covalently link to the linker separately, i.e., the protein-cell conjugate;

(4) optionally, further comprising a step of removing the protein that does not link to the cell from the second mixture, to obtain a purified second mixture comprising the protein-cell conjugate;

Or which comprises the following steps:

(a) contacting a cell with a bifunctional cross-linking agent so that a linking group of the bifunctional cross-linking agent is covalently linked to the cell, thereby obtaining a first mixture, which comprises the cell linked to the linking group;

(b) optionally, further comprising a step of removing the unlinked bifunctional cross-linking agent from the first mixture, to obtain a purified cell linked to the linking group;

(c) contacting the cell linked to the linking group obtained in step (a) or (b) with a protein, so that the linking group covalently links to the protein, thereby obtaining a second mixture, which comprises a conjugate of the protein and the cell which covalently link to the linker separately, i.e., the protein-cell conjugate;

(d) optionally, further comprising a step of removing the protein that does not link to the cell from the second mixture, to obtain a purified second mixture comprising the protein-cell conjugate;

preferably, the cell has free sulfhydryl groups distributed on its surface, when the cell is not linked to the linker preferably, the bifunctional cross-linking agent comprises both a group capable of reacting with amino group and a group capable of reacting with sulfhydryl group.

According to the method of any item of the second aspect of the present invention, the cell is a cell with immunologic function; preferably, the cell is at least one selected from the group consisting of lymphocytes, monocytes, macrophages, dendritic cells, and natural killer cells.

In some embodiments of the present invention, the bifunctional cross-linking agent comprises both a succinimidyl group and a maleimidyl group. Any compounds comprising both succinimidyl group and maleimidyl group can fulfill the present invention.

In some specific embodiments of the present invention, the bifunctional cross-linking agent includes but is not limited to succinimidyl 4-(N-maleimidomethyl)-cyclohexane-1-carboxylate (SMCC) or analogues thereof, N-succinimidyl-4-(N-maleimidomethyl)-cyclohexane-1-carboxy-(6-aminocaproate), which is a long-chain analogue of SMCC (LC-SMCC), (N-maleimidomethyl)-cyclohexane-1-carboxylic acid-3-sulfosuccinimide ester (sulfonic acid group SMCC, SULFO-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimidyl ester (EMCS), meta-maleimidobenzoyl-N-hydroxysuccinimide ester (MBS), N-(α-maleimidoacetoxy)-succinimide ester (AMAS), succinimidyl-6-(β-maleimidopropionylamino)hexanoate (SMPH) or N-succinimidyl 4-(para-maleimidophenyl)-butyrate (SMPB).

According to the method of any item of the second aspect of the present invention, the succinimidyl of the bifunctional cross-linking agent reacts with a free amino group of the protein to form an amido linkage, and the maleimidyl of the bifunctional cross-linking agent reacts with a free sulfhydryl group on the cell to form a thioether linkage.

According to the method of any item of the second aspect of the present invention, the protein includes but is not limited to antigen proteins (e.g., tumor associated antigens, antigens associated with infectious diseases, antigens associated with autoimmune diseases), epitopes, antibodies, hormones, growth factors, vitamins, colony stimulating factors.

In an embodiment of the present invention, the protein is keyhole limpet hemocyanin (KLH); in another embodiment, the protein is insulin. In another embodiment, the protein is liver cancer associated protein, glypican-3 (GPC3).

According to the method of any item of the second aspect of the present invention, it is characterized in one or more of the following items (1) to (4):

(1) the contacting is performed at a temperature of 4-40° C., preferably 6-37° C., more preferably 15-25° C., for example, room temperature;

(2) the contacting is performed for a time of 10-60 min, preferably 20-50 min, more preferably 30-40 min;

(3) the contacting is performed in a solution, which is for example a physiological saline solution or a buffer solution, wherein the buffer solution is for example phosphate buffer solution, citrate buffer solution, acetate buffer solution, succinate buffer solution, borate buffer solution, tartrate buffer solution, lactate buffer solution or carbonate buffer solution;

(4) the contacting is performed at a pH of 4.0-9.0, preferably 6.0-8.0, further preferably 6.5-7.5, more preferably 7.0-7.2.

In some embodiments of the present invention, the buffer solution is phosphate buffer solution (PBS).

In some embodiments of the present invention, the bifunctional cross-linking agent is dissolved in dimethyl sulfoxide.

The present invention further relates to use of the protein-cell conjugate of any one of items of the first aspect of the present invention in manufacturing of a medicament and/or vaccine, wherein the medicament and/or vaccine is used for prevention or treatment of one or more of the following diseases:

(1) diseases relevant to the protein in the protein-cell conjugate;

(2) malignant tumors;

(3) infectious diseases caused by pathogenic microorganisms;

(4) autoimmune diseases;

The present invention further relates to a method for prevention or treatment of one or more of the following diseases, (1) diseases relevant to the protein in the protein-cell conjugate;

(2) malignant tumors;

(3) infectious diseases caused by pathogenic microorganisms;

(4) autoimmune diseases;

wherein the method comprises a step of administering to a subject in such need a prophylactically or therapeutically effective amount of the protein-cell conjugate of any one of the items of the first aspect of the present invention.

The present invention is described in details as follows.

In the present invention, the protein can be either an intact protein molecule, or a polypeptide with certain function such as epitope function, and the size of the polypeptide can be 8 to 100 amino acids, wherein an amino group of the protein or polypeptide can chemically react with a bifunctional cross-linking agent to form a covalent linkage.

In the present invention, the protein includes but is not limited to antigen proteins (e.g., tumors associated antigens, antigens associated with infectious diseases, antigens associated with autoimmune diseases), epitopes, antibodies, hormones, growth factors (e.g., IL-2, IL-3, IL-4, IL-6, EGF, TGF-α, VEGF, etc.), vitamins, colony stimulating factors (e.g., G-CSF, MCSF, GM-CSF, etc.).

When the protein is an antigen protein or an antigen epitope, the antigen protein can be conveyed to lymphatic tissue via the cell in the protein-cell conjugate, so as to improve the targeting ability of the antigen protein.

When the protein is an antibody, a hormone, a growth factor, etc., a killer cell can be conveyed to a target cell by utilizing the targeting ability of the antibody, etc., so as to improve the killing effect on the target cell. For example, tumor specific cytotoxic T cells can be brought to tumor by recognition of the surface antigen of tumor cells by an antibody, so as to improve the killing and scavenging effects of the cytotoxic T cells on tumor cells.

In some embodiments of the present invention, the antibody is a monoclonal antibody.

In the present invention, the antibody can be either an intact antibody, or its antigen binding site.

In the present invention, the cell is preferably a cell which has free sulfhydryl groups distributed on its surface, and the sulfhydryl groups can chemically react with a bifunctional cross-linking agent to form covalent linkages. It is well known by those skilled in the art that cells having sulfhydryl groups distributed on its surface include: lymphocytes (e.g., B cells, T cells), monocytes, macrophages, NK cells, dendritic cells, etc., (Matthias T Stephan, James J Moon, Soong Ho Um, et al. Therapeutic cell engineering with surface-conjugated synthetic nanoparticles. Nature Medicine, 2010, 16 (9), 1035-1042). These cells can be derived from blood (e.g., peripheral blood), or separated and obtained from tissues.

In the present invention, the cell can be a living cell or a dead cell (an apoptotic cell).

In the present invention, the cell can be a single kind of cells, or a mixture of a plurality of kinds of cells, for example, can be a mixture of T lymphocytes and B lymphocytes, or further comprise monocytes or other cellular components.

In the present invention, the method for separating and culturing the cell is well known in the art, for example, the cells can be separated from peripheral blood, or separated from bone marrow, or separated from tissues.

In some embodiments of the present invention, the cells are separated from a spleen, and the obtained spleen cells mainly comprise lymphocytes.

In the present invention, the linker in the protein-cell conjugate is a linking group formed after chemical reaction of a bifunctional cross-linking agent with a protein and a cell, respectively.

In the present invention, the bifunctional cross-linking agent refers to a compound comprising both a group capable of coupling to a protein (i.e., forming covalent linkage with a protein) and a group capable of coupling to a cell (i.e., forming covalent linkage with a cell).

In some embodiments of the present invention, the group capable of reacting with amino group can be used to couple the bifunctional cross-linking agent to a protein, while the group capable of reacting with sulfhydryl group can be used to couple the bifunctional cross-linking agent to a cell (see: FIG. 1).

In some embodiments of the present invention, the bifunctional cross-linking agent comprises both succinimidyl group and maleimidyl group, in which the succinimidyl group is used to couple the agent to a protein, and the maleimidyl group is used to couple the agent to a cell.

In some embodiments of the present invention, the succinimidyl group of the bifunctional cross-linking agent reacts with the free amino group of the protein to form an amide bond, while the maleimidyl group of the bifunctional cross-linking agent reacts with the free sulfhydryl group to form a thioether bond (see: FIG. 1).

In the present invention, the amide bond refers to —CO—NH—; in some embodiments of the present invention, the amide bond refers to a linkage formed by "click" chemical reaction between the succinimidyl group of SMCC and the free amino group of a protein molecule.

In the present invention, the thioether bond refers to $R^1$—S—$R^2$, wherein R is an organic group; in some embodiments of the present invention, the thioether bond refers to a covalent bond formed between the maleimidyl group and the free sulfhydryl group on cell membrane.

Other bifunctional cross-linking agents that are well known in the art but are not listed in the present invention, for example, cross-linking agents comprising both succinimidyl and maleimidyl groups, can also be used in the present invention.

In the present invention, the method for preparing the protein-cell conjugate comprises: a step of coupling a protein to a bifunctional cross-linking agent, and then a step of coupling the protein conjugated with the bifunctional cross-linking agent to a cell; preferably, further comprises a step of removing unlinked bifunctional cross-linking agent before coupling the protein to the cell, or preferably, further comprises a step of removing free protein coupled to the bifunctional cross-linking agent after coupling the protein to the cell; or the method comprises: a step of coupling a cell to a bifunctional cross-linking agent, and then a step of coupling the cell coupled to the bifunctional cross-linking agent to a protein; preferably, further comprises a step of removing unlinked bifunctional cross-linking agent before coupling the cell to the protein, or preferably, further comprises a step of removing unlinked protein after coupling the cell to the protein.

In the present invention, a protein can be firstly coupled to a bifunctional cross-linking agent, then the protein conjugated with the bifunctional cross-linking agent is coupled to a cell; or a cell can be firstly coupled to a bifunctional cross-linking agent, then a protein is coupled to the cell conjugated with the bifunctional cross-linking agent.

In the present invention, the process of removing unlinked bifunctional cross-linking agent includes those process well known in the art, and can be chosen according to the size of the conjugate, for example, it can be tangential flow filtration (TFF), adsorption chromatography such as high pressure liquid chromatography, adsorption filtration, selective precipitation or dialysis.

In the present invention, the process of separating cells from free proteins is well known in the art, for example, the protein in cell-containing solution can be removed by centrifugation.

In some embodiments of the present invention, the coupling reaction between the bifunctional cross-linking agent and the protein or cell is performed in a solution. The reaction solution can be chosen according to properties of the protein and the cell by a skilled person in the art. In some embodiments of the present invention, the reaction is performed in a phosphate buffer solution. In some embodiments of the present invention, the bifunctional cross-linking agent is dissolved in dimethyl sulfoxide.

In the present invention, the term "coupling" refers to forming a covalent linkage via chemical reaction between two molecules or between a molecule and a cell.

In the present invention, the buffer solution refers to a solution which is prepared from a buffer pair consisting of "weak acid and its conjugate base" or "weak base and its conjugate acid", and is capable of reducing pH change when an amount of other substance is added.

In the present invention, the diseases associated with the protein can be for example tumor-antigen protein associated tumors, or infectious diseases relating to known specific surface antigen proteins of pathogenic microorganisms, or autoimmune diseases relating to autoantigen proteins or other diseases which are known to relate to a protein and can be prevented or treated by stimulating immune response to the protein or inducing immune tolerance to the protein.

In some embodiments of the present invention, the antigen is a cancer antigen. As used herein, "cancer antigen" is a compound relating to tumor or cancer cell surface, for example, a peptide or a protein, and when the antigen is expressed on the surface of an antigen presenting cell, it can provoke an immune response. Cancer antigens can be obtained from cancer cells by preparing crude extract of cancer cells, for example, as described in Cohen P A, et al., (1994) Cancer Res 54: 1055-8, by partially purifying the antigens, by recombination technology, or by de novo synthesis of a known antigen. Cancer antigens include but are not limited to antigens that are recombinantly expressed, an immunogenic part of tumor or cancer, or a whole tumor or cancer. These antigens can be isolated or prepared recombinantly or by any other methods known in the art.

The terms "cancer antigen" and "tumor antigen" can be used interchangeably, and refer to antigens differentially expressed by cancer cells and can thereby be exploited to target cancer cells. Cancer antigens are antigens capable of stimulating significant tumor-specific immune response. Some of these antigens are encoded by normal cells, although not necessarily expressed. These antigens can be characterized as those which are normally silent (i.e., not expressed) in normal cells, those that are expressed only at certain stages of differentiation, and those that are temporally expressed (e.g., embryonic antigens and fetal antigens). Other cancer antigens are encoded by mutant genes, such as oncogenes (e.g., activated ras oncogenes), suppressor genes (e.g., mutant p53), or are fused proteins resulting from internal deletions or chromosomal translocations. Still other cancer antigens can be those encoded by virus genes such as those carried by RNA and DNA tumor viruses. Examples of tumor antigen include MAGE, MART-1/Melan-A, gp100, dipeptidyl peptidase IV (DPPIV), adenosine deaminase-binding protein (ADAbp), cyclophilin b, colorectum-associated antigen (CRC)-C017-1A/GA733, carcino-embryonic antigen (CEA) and its immunogenic epitopes CAP-1 and CAP-2, etv6, am11, prostate-specific antigen (PSA) and its immunogenic epitopes PSA-1, PSA-2, and PSA-3, prostate-specific membrane antigens (PSMA), T-cell receptor/CD3-ζ chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B 3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-uvomorulin, α-catenin, β-catenin and γ-plakoglobin, p120ctn, gp100$^{Pme1117}$, PRAME, NY-ESO-1, cdc27, adenomatous multiplepolyposis coli protein (APC), calspectin, connexin 37, Ig-idiotype, p15, gp75, GM2 and GD2 gangliosides, viral products such as proteins of human papilloma virus, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7 and c-erbB-2.

Cancers or tumors and tumor antigens associated with such tumors (but not exclusively) include acute lymphoblastic leukemia (etv6; am11; cyclophilin b), B cell lymphoma (Ig-idiotype), neuroglioma (E-uvomorulin; α-catenin; β-catenin; γ-plakoglobin; p120ctn), bladder cancer (p21ras), biliary cancer (p21ras), breast cancer (MUC family; HER2/neu; c-erbB-2), cervical cancer (p53; p21ras), colon cancer (p21ras; HER2/neu; c-erbB-2; MUC family), colorectal cancer (colorectal-associated antigens (CRC)-C017-1A/GA733; APC), choriocarcinoma (CEA), epithelial cell cancer (cyclophilin b), gastric cancer (HER2/neu; c-erbB-2; ga733 glucoprotein), hepatocellular cancer (α-fetoprotein), Hodgkin lymphoma (1mp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung cancer (HER2/neu; c-erbB-2), nasopharyngeal cancer (1mp-1; EBNA-1), ovarian cancer (MUC family; HER2/neu; c-erbB-2), prostate cancer (prostate-specific antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glucoprotein), renal cancer (HER2/neu; c-erbB-2), squamous cell cancers of cervix and oesophageal (viral products such as human papilloma virus proteins), testicular cancer (NY-ESO-1), T-cell leukemia (HTLV-1 epitope), and melanoma (Melan-A/MART-1; cdc27; MAGE-3; p21ras; gp100$^{Pme1117}$).

In some embodiments of the present invention, the malignant tumors include but are not limited to skin basal cell cancer, biliary tract cancer, bladder cancer, bone cancer, brain and CNS cancer, breast cancer, cervical cancer, choriocarcinoma, colorectal cancer, connective tissue cancers, cancers of digestive system, endometrial cancers, esophageal cancer, eye cancer, head and neck cancers, stomach cancer, neoplasm in epithelial cells, kidney cancer, larynx cancer, leukemia, liver cancer, lung cancer (e.g., small cell and non-small cell lung cancers), lymphoma including Hodgkin and non-Hodgkin lymphomas, melanoma, myeloma, neuroblastoma, mouth cancers (e.g., lip, tongue, oral cavity cancers), ovarian cancer, pancreatic cancer, prostate cancer, retinoblastoma, rhabdomyosarcoma, rectal cancer, renal cancer, respiratory system cancers, sarcomas, skin cancer, gastric cancer, testicular cancer, thyroid cancer, uterine cancer, urinary system cancer, and other cancers and sarcomas. The tumor-associated antigens can be for example a-fetoprotein of liver cancer, tyrosinase-related protein-2 of melanoma, etc.

In the present invention, the infectious diseases can be for example infectious diseases relating to bacteria, fungi, viruses and parasites.

The viruses include but are not limited to: Retroviridae (e.g., human immune defective viruses, such as HIV-1 (also referred to as HDTV-III), LAVE or HTLV-III/LAV, or HIV-III, as well as other isolates, for example, HIV-LP; Picornaviridae (e.g., polio viruses, hepatitis A viruses; enteroviruses, human coxsackie viruses, rhinoviruses, human enteric orphan viruses); Calciviridae (e.g., strains that cause gastroenteritis); Togaviridae (e.g., Equine encephalitis virus, Rubella virus); Flaviridae (e.g., Dengue virus, encephalitis viruses, Yellow fever virus); Coronaviridae (e.g., coronaviruses); Rhabdoviridae (e.g., vesicular stomatitis viruses, Rabies viruses); Filoviridae (e.g., Ebola viruses); Paramyxoviridae (e.g., parainfluenza viruses, mumps viruses, measles viruses, respiratory syncytial viruses); Orthomyxoviridae (e.g., influenza viruses); Bungaviridae (e.g., Hantaan viruses, parasitic aeginetia viruses, phleboviruses and nairo viruses); Arenaviridae (hemorrhagic fever viruses); Reoviridae (e.g., reoviruses, orbiviruses and rotaviruses); Birnaviridae; Hepadnaviridae (hepatitis B virus); Parvoviridae (parvoviruses); Papovaviridae (papilloma viruses, polyoma viruses); Adenoviridae (most adenoviruses); Herpesviridae (herpes simplex viruses (HSV)1 and 2, varicella herpes zoster viruses, cytomegalovirus (CMV), herpes virus; Poxviridae (variola virus, cowpox virus, poxvirus); and Iridoviridae (e.g., African swine fever virus); as well as unclassified virus (e.g., A hepatitis factors (thought to be a defective trabants of hepatitis B virus), non-A non-B hepatitis factors (class 1=internal transmitted; class 2=parenterally transmitted (i.e., hepatitis C); Norwalk virus and related viruses, as well as astroviruses).

The bacteria include Gram-negative and Gram-positive bacteria, both of which can be used as antigens in vertebrates. Gram-positive bacteria include but are not limited to *Pasteurella* species, *Staphylococcus* species, and *Streptococcus* species. Gram-negative bacteria include but are not limited to *Escherichia coli*, *Pseudomonas* species, and *Salmonella* species. Examples of infectious bacteria include but are not limited to *Helicobacter pyloris*, *Borrelia burgdorferi*, *Legionella pneumophila*, *Mycobacteria* sp. (e.g., *Mycobacterium tuberculosis*, *Mycobacterium avium*, *Mycobacterium intracellulare*, *Mycobacterium kansasii*, *Gordon mycobacterium*), *Staphylococcus aureus*, *Neisseria gonorrhoeae*, *Neisseria meningitidis*, *Listeria monocytogenes*, *Streptococcus pyogenes* (Group A *streptococcus*), *Streptococcus agalactiae* (Group B *streptococcus*), *Streptococcus* (viridans group), *Streptococcus faecalis*, *Streptococcus bovis*, *Streptococcus* (anaerobius), *Streptococcus pneumoniae*, pathogenic *Campylobacter* sp., *Enterococcus* sp., *Haemophilus influenzae*, *bacillus anthracis*, *Corynebacterium diphtheriae*, *Corynebacterium* sp., *Erysipelothrix rhusiopathiae*, *Clostridium perfringens*, *bacillus tetani*, *Enterobacter aerogenes*, *Klebsiella*, *Pasteurella multocida*, *bacteroides* sp., *Fusobacterium nucleatum*, *Streptobacillus moniliformis*, *Treponema pallidum*, *Treponema pertenue*, *Leptospira*, *Rickettsia*, *Actinomyces Israeli*.

Examples of fungi include *Cryptococcus neoformans*, *Histoplasma capsulatum*, *Coccidioides immitis*, *Blastomyces dermatitidis*, *Chlamydia trachomatis*, *Candida albicans*.

Examples of parasites include *Plasmodium* spp. such as *Plasmodium falciparum*, *Plasmodium malariae*, *Plasmodium ovale*, *Plasmodium vivax*, as well as *Toxoplasma gondii*. Blood-porne and/or tissues parasites include *Plasmodium* spp., *Babesia microti*, *Babesia divergens*, *Leishmania tropica*, *Leishmania* spp., *Leishmania Braziliensis*, *Leishmania donovani*, *Trypanosoma gambiense*, *Trypanosoma rhodesiense* (African sleeping sickness), *Trypanosoma cruzi* (Chagas' disease), and *Toxoplasma gondii*.

most of protein antigens relating to infectious diseases have been disclosed. For example, surface antigen proteins of hepatitis B, HIV-associated proteins of AIDS, membrane proteins of most bacteria, wall-held proteins of fungi, parasite proteins of different stages of development process of parasites.

In the present invention, the autoimmune diseases include but are not limited to rheumatoid arthritis, ankylosing spondylitis, variable skin diseases, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., Pemphigus Vulgaris), Grave's disease, autoimmune hemolytic anemia, autoimmune Thrombocytopenic Purpura, scleroderma with anti collagen antibodies, mixed connective tissue disease, polymyositis, pernicious anaemia, idiopathic Addison's disease, autoimmune-associated sterility, glomerulonephritis (e.g., crescent glomerulonephritis, proliferative glomerulonephritis), bullous pemphigoid, Sjogren's syndrome, insulin resistance, and autoimmune diabetes mellitus, etc. The autoantigens relating to some autoimmune diseases are disclosed, for example, islet beta-cell antigen of type I diabetic pancreas, nerve sheath cell antigens of multiple sclerosis, Pso p27 of psoriasis, hsp90 of Rheumatoid arthritis, CUZD1 and JP2 of Crohn's disease, etc.

In the present invention, living cells or apoptotic cells can be used according to purpose of using cells. For example, when human immune response is to be activated for prevention or treatment of tumors or infectious diseases, living cells can be used; while when immune tolerance against autologous or extraneous antigens is to be induced for prevention or treatment of autoimmune diseases, apoptotic cells can be used (because stable apoptotic cells have properties of inducing immune tolerance).

The method for preparing the apoptotic cells is well known in the art, for example, the cells coupled with protein can be irradiated with ultraviolet ray to produce apoptotic cells.

In the present invention, for the above uses, autologous cells or allogeneic cells can be used. Autologous cells are preferably used for prevention or treatment of autoimmune diseases.

In the present invention, the subject refers to a mammal, for example, human, dog, monkey, mouse, rat, bovine, equine, etc.

In the present invention, the effective amount refers to a dose that can achieve treatment, prophylaxis, alleviation and/or relief of the diseases or disorders as disclosed in the present invention.

Beneficial Effects of the Invention

In the present invention, a bifunctional cross-linking agent is used to couple a protein and a cell conveniently and effectively, to obtain a protein-cell conjugate, which can be used for many purposes according to the properties of the protein and the cell of the obtained conjugate, for example, the target ability or antigen presentation of the cell can be utilized to exert the better immunization of protein, and in the meantime, since a very small amount of protein carried by the cell can achieve a similar or better effect than a large amount of free soluble protein used for direct immunization, side-effects of direct immunization with large amount of protein can be avoided.

SPECIFIC MODE FOR CARRYING OUT THE INVENTION

The embodiments of the present invention are described in details as follows in conjunction with examples, but those skilled in the art would understand that the following examples are used for illustrating the present invention only, rather than limiting the scope of the present invention. In the examples, if specific conditions are not given, conventional conditions or conditions suggested by manufacturers would be applied. The reagents or instruments without marked with manufacturers were conventional products commercially available in market.

Example 1

Coupling of antigen to succinimidyl 4[N-maleimidomethyl]cyclohexane-1-carboxylate (SMCC)

1) A tool antigen Keyhole Limpet Hemocyanin (KLH) (ThermoscientificCompany, Art. No. 77653) was taken and prepared with PBS solution to form 10 mg/ml solution, and SMCC (ThermoscientificCompany, USA, Art. No. 22360) was taken and mixed with dimethylsulfoxide to form 10 mM solution. 0.3 ml KLH solution and 30 μl of the above SMCC solution were placed in 3 ml PBS reaction system, incubated at room temperature for 30 min, and after reaction the protein was then subjected to an assay for determining SMCC linking efficiency.

Figure 1:
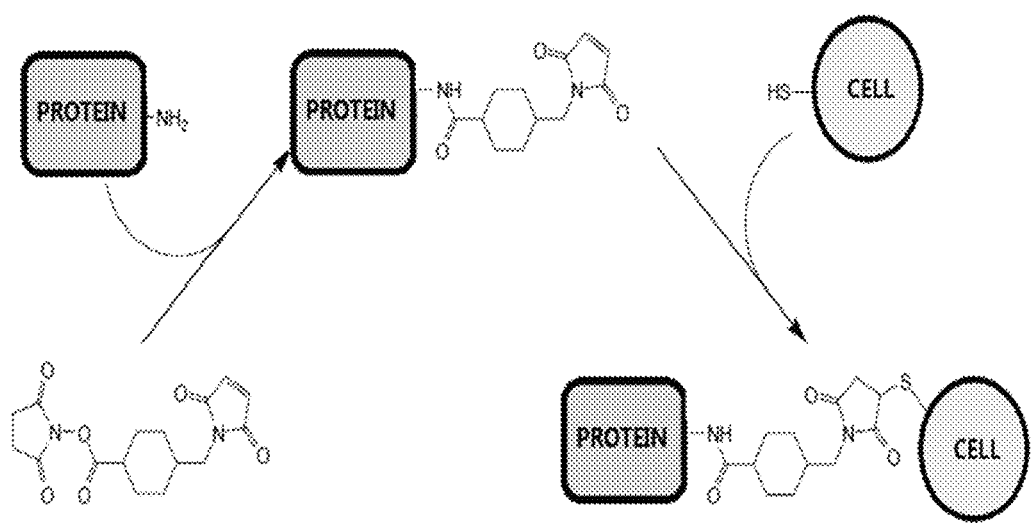
FIG. 1 shows a schematic diagram of coupling a protein and a cell to SMCC, in which "protein" refers to a protein molecule, "cell" refers to a cell.
Figure 2:
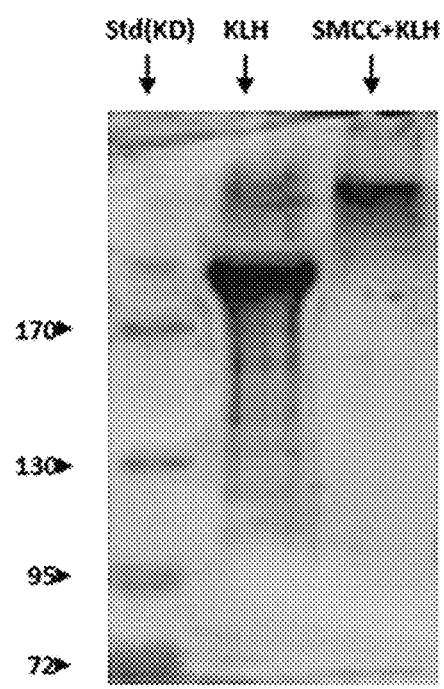
FIG. 2 shows results of SDS-polyacrylamide gel electrophoresis after coupling KLH to SMCC.

2) Determination of SMCC linking efficiency by protein electrophoresis: the above protein after reaction was subjected to SDS-polyacrylamide gel electrophoresis, KLH protein was used as a control, and the results were shown in FIG. 2. It could be seen that the molecular weight at position of SMCC-KLH band increased significantly in comparison with that position of KLH band, the tailing phenomena below the SMCC-KLH band might be due to the fact that a small portion of amino groups of KLH were still not saturated by SMCC, and this could be improved by increasing SMCC concentration.

Figure 3:
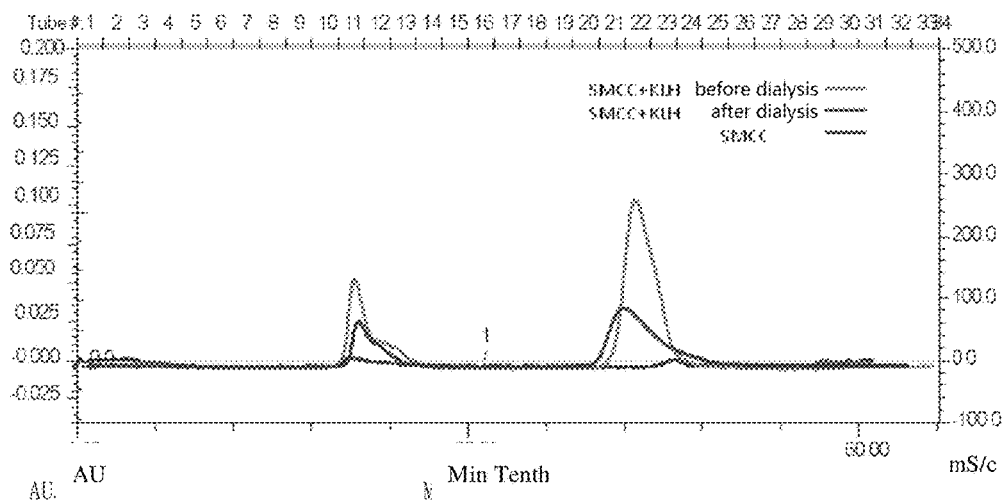
FIG. 3 shows results of high pressure liquid chromatography before and after dialysis of the reaction system of KLH and SMCC; the left peak is KLH peak, the right peak is SMCC peak; in which the three curves for the left peak from top to bottom in order are SMCC+KLH before dialysis, SMCC+KLH after dialysis, SMCC, the three curves for the right peak from top to bottom in order are SMCC+KLH before dialysis, SMCC, SMCC+KLH after dialysis; the left ordinate is absorbance of UV (AU), the bottom abscissa is retention time (Min Tenth), unit is min, the right ordinate is conductivity, unit is millisiemens/cm (mS/cm), the top abscissa is tube number.

3) Removal of free SMCC: SMCC was small molecular substance, and thus free SMCC would inevitably exist in KLH-SMCC reaction system, however, the free SMCC would seriously influence the coupling of KLH-SMCC and cell. The solution obtained after step 1) was dialyzed with 2 L PBS solution overnight at room temperature. After dialysis, the protein solutions before and after dialysis were subjected to high pressure liquid chromatography, and the results were shown in FIG. 3. It could be seen that SMCC peak substantially disappeared after dialysis, indicating that the free SMCC was substantially removed. The protein after dialysis was freeze-dried and stored at −80° C.

Example 2

Coupling of KLH-SMCC to Mice Splenocytes

Figure 4:
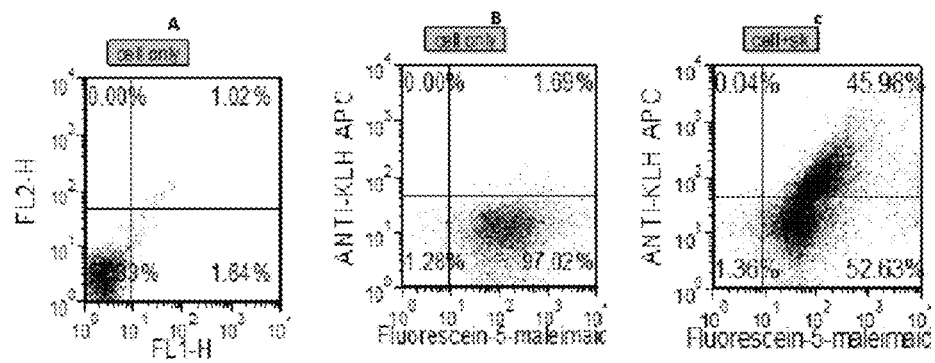
FIG. 4 shows results of flow cytometry for detecting sulfhydryl distribution on surface of mice splenocytes, in which A refers to cells without any staining (negative control), B refers to cells that are not coupled to SMCC-KLH and are stained with fluorescein-linked maleimide (reflecting sulfhydryl level of cell surface), C refers to cells coupled to SMCC-KLH and stained with fluorescein-linked maleimide and stained with anti-KLH-APC (because SMCC occupies some sulfhydryl groups, fluorescein-linked maleimide staining is weakened).

1) Distribution of sulfhydryl groups on splenocyte surfaces:

Firstly, splenocytes were prepared. Fresh spleen was taken from Balb/c mice, placed in small vessel with clouded glass surface, then gently ground using pestle with clouded glass surface, so as to prepare a cell homogenate of spleen. Red cells were then lysed with erythrocytolysis solution (BD Company, USA, Art. No. 349202) to obtain mononuclear cells of spleen. The mononuclear cells of spleen (in which lymphocytes were about 95% or more) were washed with PBS solution, and resuspended in PBS solution. The sulfhydryl distribution on surface of the mononuclear cells of mice spleen was measured with maleimide-fluorescein agent (Fluorescein-5 maleimide, maleimide-FL, ANA Spec Company, Art. No. 81405), and the specific method comprised: incubating the maleimide-FL reagent (according to the specification of manufacturer) with spleen cells at room temperature for 30 min, so that maleimidyl group reacted with sulfhydryl groups on cell membrane. The cells were washed with PBS solution twice, then fluorescence intensity was measured with flow cytometer. The fluorescence intensity represented sulfhydryl density on cell membrane surface, and the results were shown in FIG. 4.

2) Coupling of KLH-SMCC to mice splenocytes and assay thereof:

Mice splenocytes ($1 \times 10^7$) and KLH-SMCC as prepared in Example 1 in ratio of $1 \times 10^7$ splenocytes/0.2 mlPBS/0.2 mg KLH-SMCC (0.2 mg referred to the amount of KLH) were subjected to interaction at room temperature for 30 min, washed with PBS solution twice to remove KLH-SMCC that were not linked to cells. Thereafter, anti-KLH-APC (BD Company, USA, Art. No. 560720) and maleimide-fluorescein were used for staining to measure KLH coupled on cell membrane and free sulfhydryl on cell surface respectively, and the results were shown in FIG. 4, which showed KLH-SMCC could be effectively coupled to cells to obtain KLH-coupled splenocytes (KLH-SMCC-splenocytes).

Figure 5:
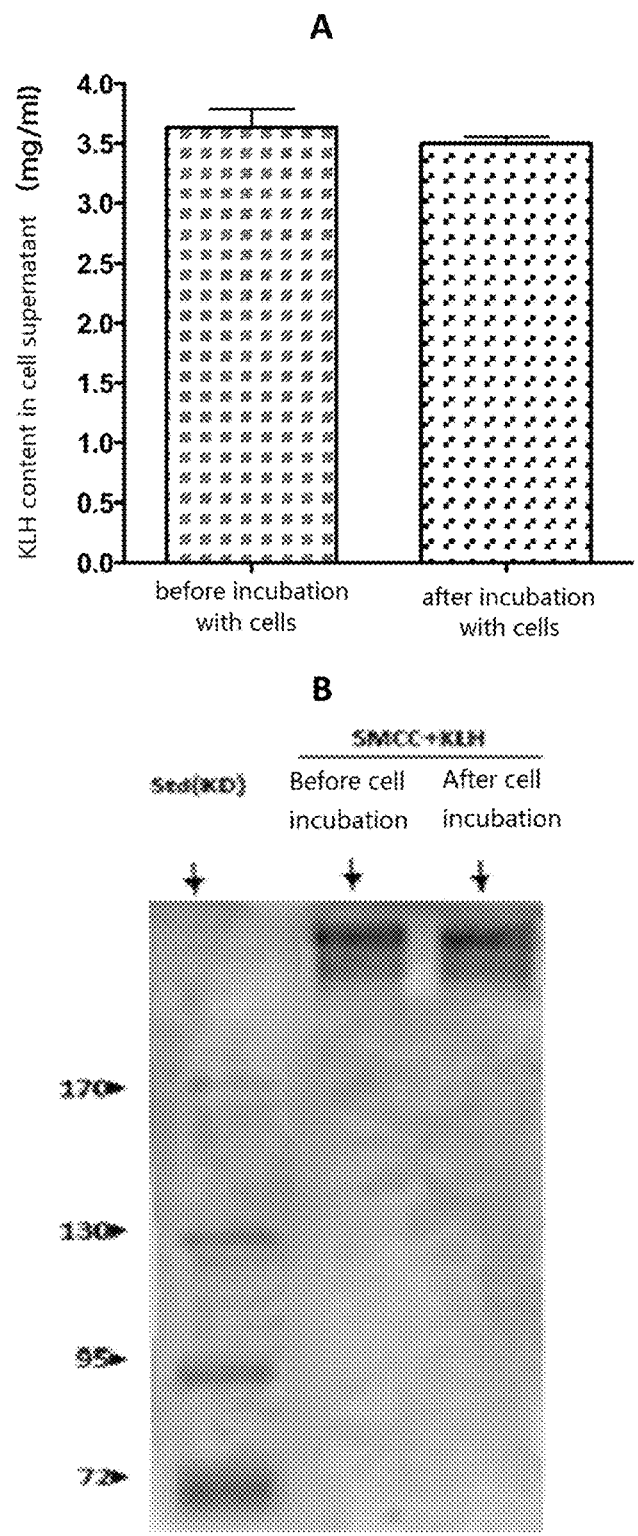
FIG. 5 shows protein content in supernanants pre- and post-coupling (A) and results of SDS-polyacrylamide gel electrophoresis before and after coupling KLH-SMCC to splenocytes(B).

3) In order to further verify whether KLH was coupled to cells, the solutions before and after cell reaction were subjected to ELISA assay for protein content (protein concentration assay kits were from ThermoScientific Company, Art. No. 23225), and the results showed that the protein content was slightly reduced after reaction, that was, the KLH protein concentration in the supernatant was 3.633±0.088 mg/ml before cell reaction, and the KLH protein concentration in the supernatant was 3.50±0.058 mg/ml after reaction, indicating that KLH was coupled to cells (FIG. 5A). The amount of protein coupled to cells could be calculated by the following formula: ((3.633−3.50)/3.633)×0.2 mg (actual SMCC-KLH content in solution before reaction)=0.0074 mg, therefore, the amount of protein linked to $1 \times 10^7$ splenocytes was about 0.0074 mg. The solutions before and after cell reaction were subjected to SDS-PAGE electrophoresis, and the results were consistent with the results of ELISA. As shown in FIG. 5B, the density of electrophoresis bands after reaction was not significantly different from that before reaction, which indicated there was a small amount of protein coupled to the cells.

Example 3

Assay of Activity of KLH-Coupled Splenocytes

1) Immune Response to KLH Induced by KLH-Coupled Splenocytes

Figure 6:
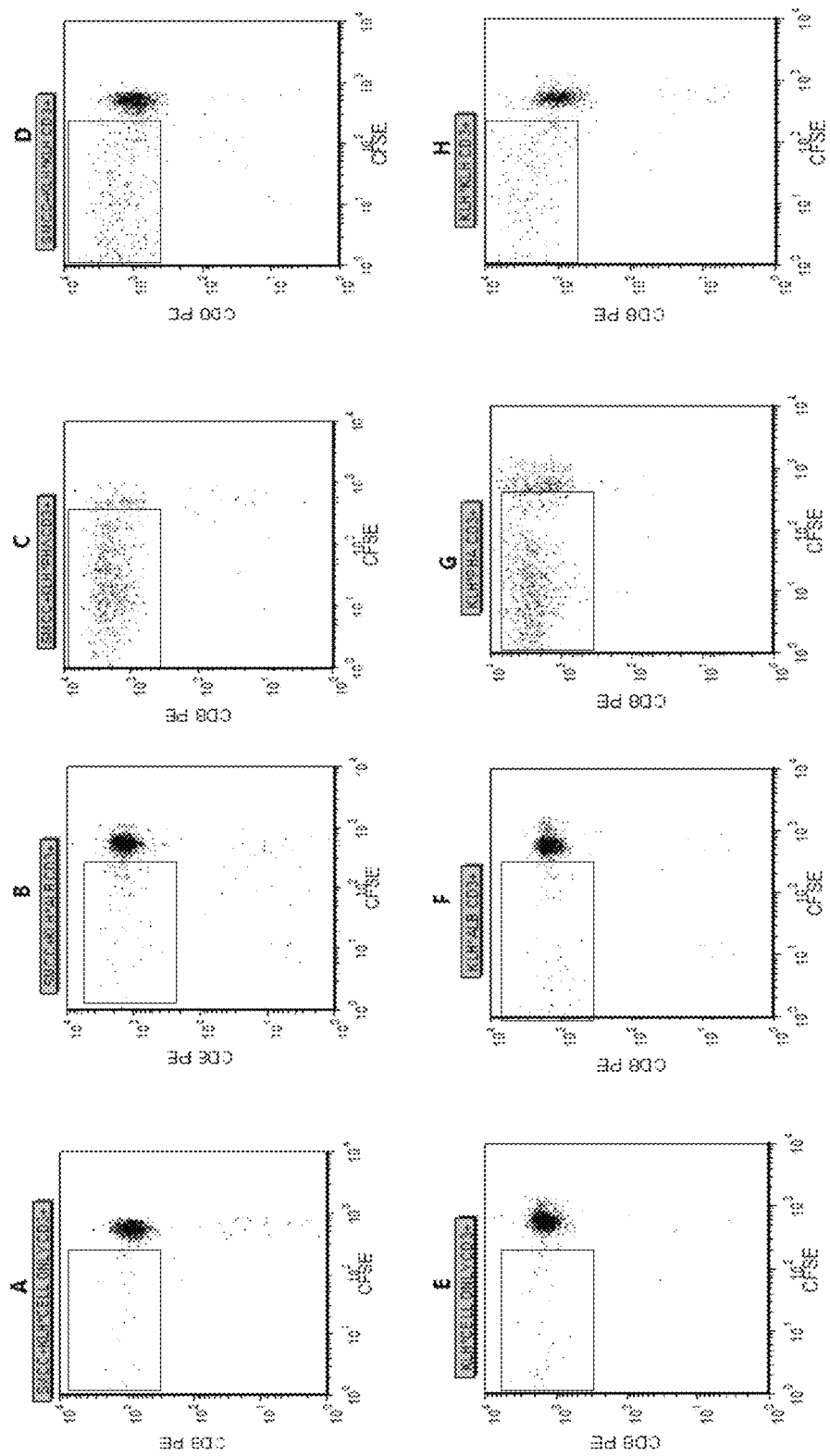
FIG. 6 shows results of comparative flow cytometry of immune response induced by immunizing animals with KLH-SMCC-splenocytes and KLH, in which A refers to splenocytes of mice immunized with KLH-SMCC-splenocytes, which are not subjected to any other in vitro stimulation (except culture solution), B refers to splenocytes of mice immunized with KLH-SMCC-splenocytes, which are subjected to in vitro stimulation of nonspecific protein-human albumin (ALB) (negative control), C refers to splenocytes of mice immunized with KLH-SMCC-splenocytes, which are subjected to in vitro stimulation of phytohemagglutinin (PHA) (positive control), D refers to splenocytes of mice immunized with KLH-SMCC-splenocytes with in vitro stimulation of KLH, E refers to splenocytes of mice immunized with KLH without any in vitro stimulation, F refers to splenocytes of mice immunized with KLH with in vitro stimulation of ALB, G refers to splenocytes of mice immunized with KLH with in vitro stimulation of PHA, H refers to splenocytes of mice immunized with KLH with in vitro stimulation of KLH.

The KLH-coupled splenocytes prepared in Example 2 (KLH-SMCC-splenocytes) in number of $1 \times 10^7$ (the amount of KLH coupled to the cells was about 0.0074 mg) was given to a mouse via tail intravenous injection, while the control was given 0.4 mg KLH via intraperitoneal injection; another control group was given $1 \times 10^7$ uncoupled splenocytes via tail intravenous injection (3Balb/c mice for each group). The injection was preformed once per week, for two weeks; the mice were executed one week after the second injection, and the splenocytes of mice were taken for immunologic assay. The mice splenocytes were stained with carboxyfluorescein diacetate succinimidyl ester (CFSE, Invitrogen Company, Art. No. C34554), and the staining method comprised the following steps: 1 μM CFSE was added to 2 ml cell solution containing $2 \times 10^7$ cells, staining was performed at 37° C. for 10 min, then the cells were washed by centrifugation with 10 ml PBS solution at 1200 rpm twice, and then the cells were resuspended in cell culture solution for subsequent cell culture. The stained splenocytes ($1 \times 10^6$/well) were cultured with stimulation of KLH(10 μg/ml), human albumin (ALB, 10 μg/ml) (Baxten Company, Art. No.VNAIM068), PHA (10 μg/ml) (Sigma Company, Art. No.: L-8754) and RPMI1640 culture medium containing 10% fetal calf serum (GIBCO Company), respectively for 4-5 days, then division and proliferation of T-cells were assayed with a flow cytometer. The more times the cells divide, the lower the fluorescence intensity of CFSE on cells is. Thus, the proliferation of cells could be determined by fluorescence intensity of CFSE. As shown in FIG. 6, the infusion of KLH-coupled splenocytes induced very strong immune response to KLH. Although the amount of KLH coupled to the cell was very small, its immune response to KLH induced thereby is even stronger than that induced by immunization with a large amount of KLH protein in animals.

2) Test of Lymphocyte Proliferation

Figure 7:
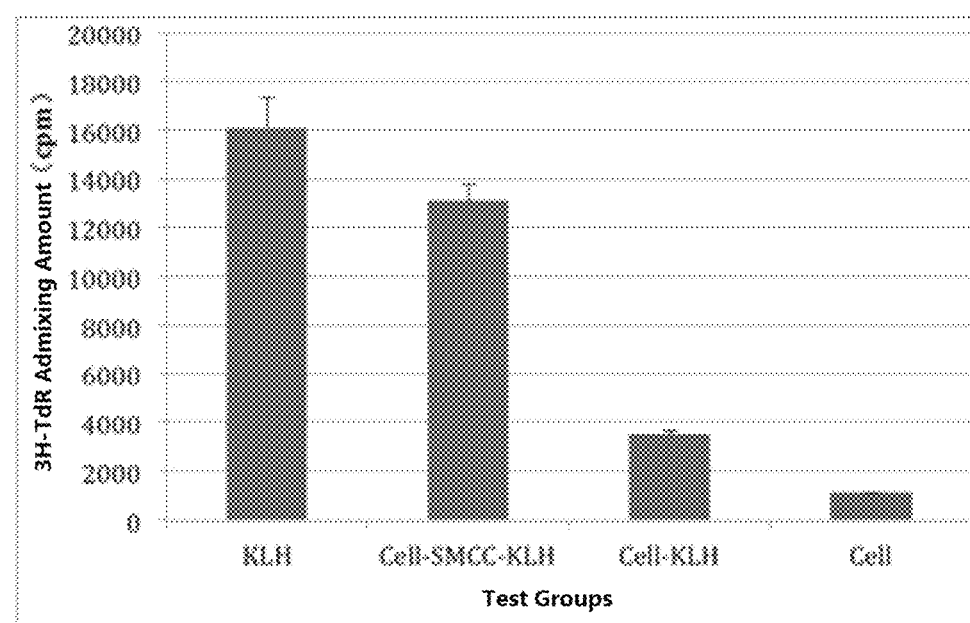
FIG. 7 shows T-cell proliferation induced by KLH-SMCC-splenocytes.

Balb/c mice (3 mice per group) were immunized with 0.2 mg KLH, $1 \times 10^7$ KLH-SMCC-splenocytes prepared in Example 2, $1 \times 10^7$ splenocytes, 0.2 mg KLH-incubated splenocytes (Cell-KLH, this group was used to observe immune effect induced by natural adhesion of KLH and cells, the incubation method comprising: reacting $1 \times 10^7$ splenocytes with 0.2 mg KLH in 0.4 ml PBS solution at room temperature for 40 min). Pure KLH 0.2 mg and $1 \times 10^7$ splenocytes were given to mice via intraperitoneal and intravenous injection, respectively, once per week for two weeks. The mice were executed one week after the last injection and splenocytes were separated. The splenocytes ($1 \times 10^6$/well) were cultured with stimulation of KLH (10 μg/ml) for 5 days, and during the last 16 hours, 3H-TdR (0.25 uCi/well) was added (3H-TdR was provided with the Laboratory of Pharmacology and Toxicology of the Academy of Military Medical Sciences, and this test was carried out by the Laboratory of Pharmacology and Toxicology of the Academy of Military Medical Sciences). A liquid scintillation analyzer was used to determine the incorporating amount of 3H-TdR (cpm). The more the value is, the more the cell proliferation is. As shown in FIG. 7, the strong T-cell response was induced in the mice subjected to treatment of KLH and KLH-SMCC-splenocytes, while the cells that were subjected to incubation of KLH but not coupled to SMCC merely induced very weak T-cell reaction in mice, which was just slightly higher than the cells without any treatment (in comparison with KLH group, p<0.01; in comparison with KLH-SMCC-splenocytes group, p<0.01).

Example 4

Figure 8:
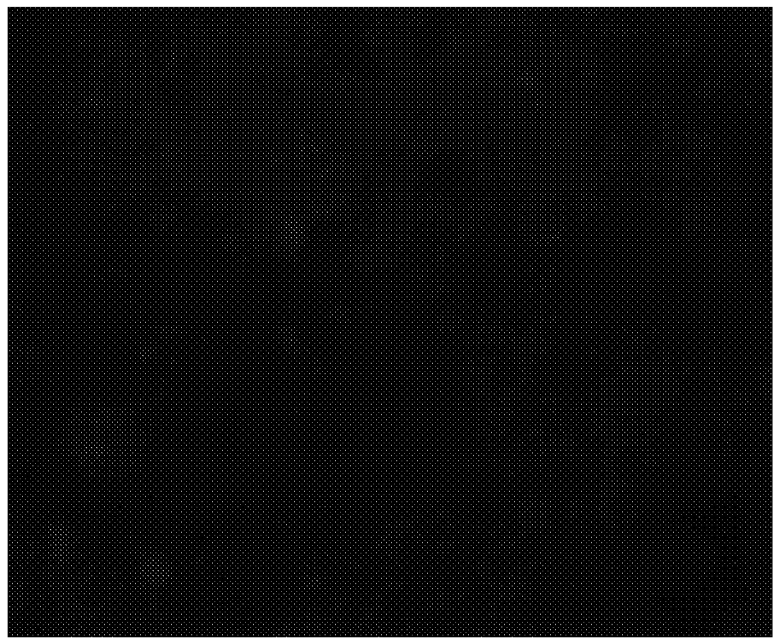
FIG. 8 shows results of the immunofluorescence assay of insulin coupled on membrane surface of SMCC-insulin-coupled splenocytes; in which A refers to splenocytes incubating with insulin, B refers to splenocytes incubating with SMCC-insulin.
Figure 8:
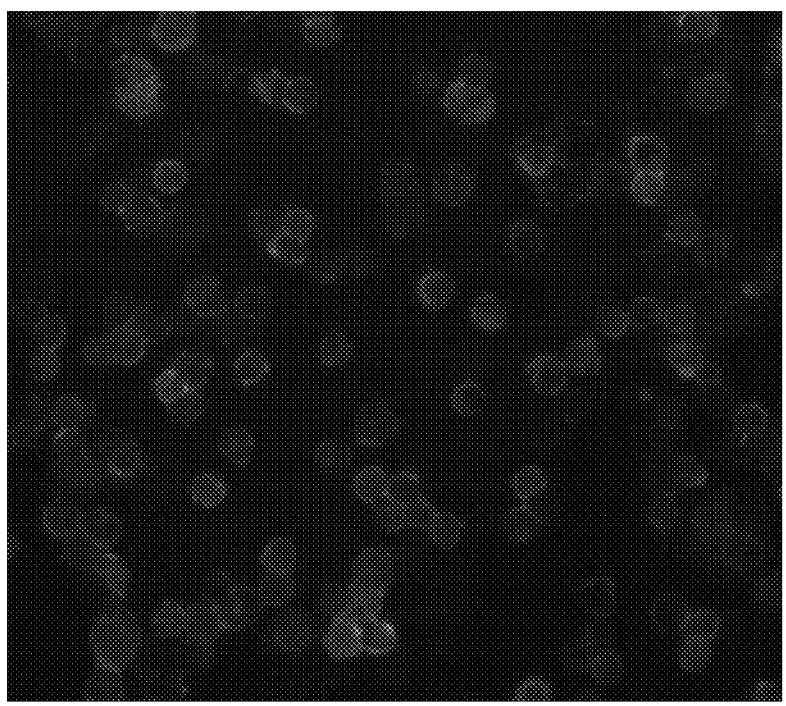

Immunofluorescence Analysis of Membrane-Coupled Insulin of Insulin-Coupled Splenocytes The process for preparing SMCC-insulin was the same as the preparation of SMCC-KLH in Example 1. Subsequently, according to the method described in Example 2, SMCC-insulin and splenocytes were incubated to obtain insulin-coupled splenocytes. Thereafter, the cells were spun on glass slides using a spinning machine, and the cells were stained by conventional immunofluorescence method, of which the specific process was referred to the instructions of insulin fluorescein staining kit (Insulin Fluorescein Staining Kit, Cosmobio Company, Japan). The control group was splenocytes incubated with insulin. It could be seen from FIG. 8 that SMCC-insulin was successfully coupled to splenocytes in very high intensity, and the circular fluorescence further indicated that the insulin was coupled to cell membrane. On the contrary, the cells of the control group were not stained, indicating that the positive staining was insulin-specific staining, rather than non-specific background staining.

Example 5

Generation of High-Titer Antibody Against Liver Cancer Antigen Glypican-3 (GPC3) Induced by Infusion of Liver Cancer-Specific Antigen GPC3-Coupled Splenocytes and Anti-Tumor Effects Thereof Antigen coupling and infusion: recombination human GPC3 antigen protein was the protein expressed and purified in the laboratory of Professor Liu's of Pathology Department of University of Florida (GPC3 protein sequence No.: AK222761, AK222766, AK300168, AK310196 or AK310689). $2 \times 10^8$ splenocytes and GPC3 protein (0.2 mg/ml) and 50 μM sulfonic SMCC (sulfo-SMCC) were incubated in 0.5 ml reaction system under shaking at room temperature for 1 hour. Then, the cells were washed twice with PBS to remove uncoupled GPC3 protein. The cells were resuspended with PBS to obtain $1 \times 10^8$/ml cell suspension. Each of Balb/c mice were subjected to intravenous injection of 200 μl GPC3-coupled splenocytes (test group) or 200 μl PBS (control group).

The Balb/c mice were subjected to intravenous injection of GPC3 antigen protein-coupled splenocytes ($2 \times 10^7$ cells/mouse). The control group was subjected to infusion of PBS solution. The infusion was performed once per week, for two weeks. After two weeks, anticoagulation blood samples were collected, and blood plasmas were prepared for assay of GPC3-specific antibody (conventional ELISA assay); in the meantime, all groups of mice were subjected to subcutaneous injection of liver cancer cell lines of syngeneic mice (1MEA, hepatic carcinoma cell line of Balb/c mice transfected with human GPC3 gene) ($2 \times 10^5$ cells/mouse), and the control group was injected with equivalent quantity of PBS. The tumor formation and growth for hepatic carcinoma cells were dynamically observed.

Figure 9:
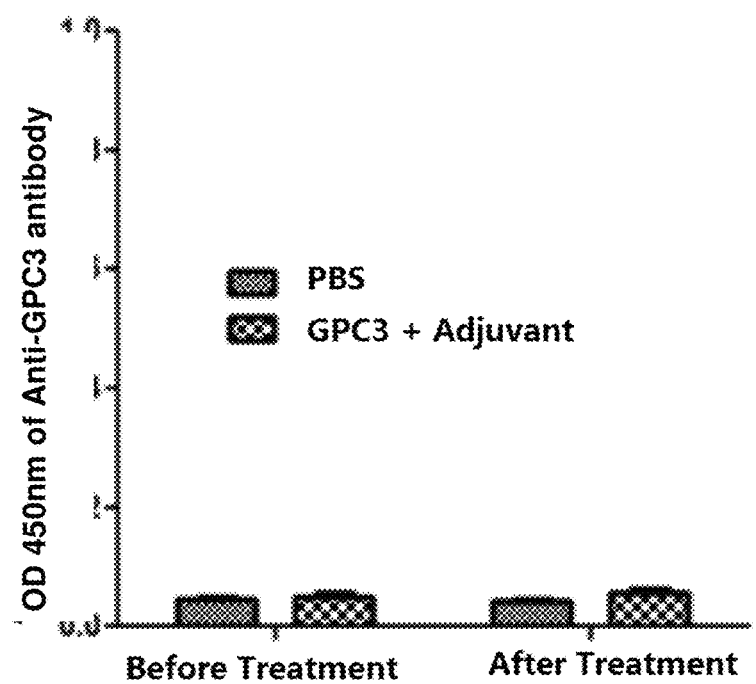
FIG. 9 shows antibody titer resulted from immunization of mice by intramuscular injection of GPC3 and adjuvant.

The infusion of GPC3-coupled splenocytes induced high level of anti-GPC3 antibody: in our previous tests, Balb/c mice were immunized with GPC3 (50 μg/times/mouse) added with Freund adjuvant via intramuscular injection, once per week for two weeks, and the antibody titers in blood plasma collected in the third week were measured. The results showed that there was not any detectable GPC3 antibody (see: FIG. 9).

Figure 10:
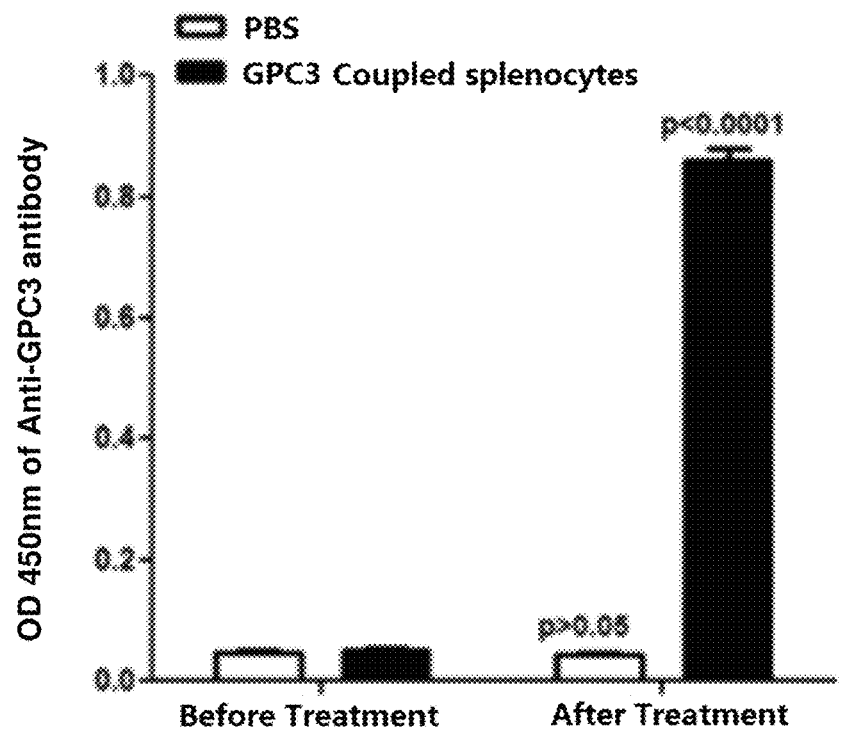
FIG. 10 shows antibody titer resulted from infusion of GPC3-coupled splenocytes in mice.

As to GPC3-coupled splenocytes for infusion, the amount of protein coupled on cell surface was very small. According to the fact that there is $10^4$ sulfhydryl groups per cell (Laurence, et al, J Leukoc Bio, 1996), $2 \times 10^7$ cells would bear $2 \times 10^{11}$ sulfhydryl groups, and if all of them were saturated, the number of the protein molecules linked to the cells was $2 \times 10^{11}$. Thus, in case of saturation, the molar of the coupled protein was: $2 \times 10^{11}/6 \times 10^{23} = 3.33 \times 10^{-13}$. The molecular weight of GPC3 was 62KD. The maximum amount protein coupled to cells was: $62 \times 1000 \times 3.33 \times 10^{-13}$ g=$2.065 \times 10^{-8}$ g=$2.065 \times 10^{-2}$ μg. Hence, the possible maximum of amount of protein that could be carried by cells and infused into body was only 1/2000 of that of intramuscular injection. However, the former could induce high level of antibody (see: FIG. 10).

Figure 11:
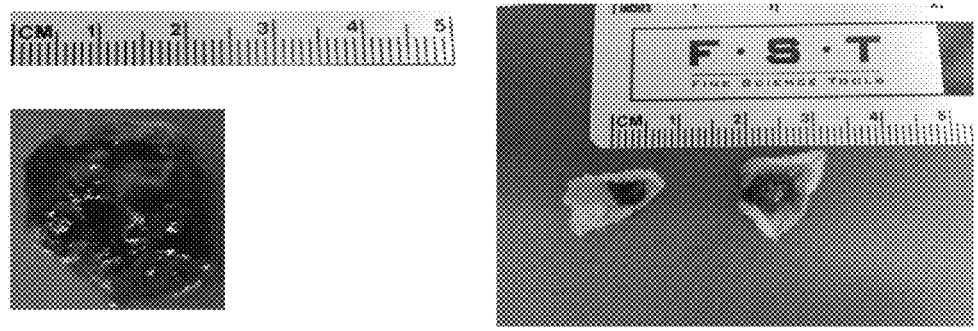
FIG. 11 shows anti-tumor effects induced by infusion of GPC3-coupled splenocytes in mice, in which the left panel refers to the control group, and the right panel refers to the GPC3-coupled splenocytes group.

The infusion of GPC3-coupled splenocytes induced very strong anti-tumor effects: after the mice were immunized for two weeks, murine hepatic carcinoma line, which highly expressed hepatic carcinoma antigen GPC3, was subcutaneously injected ($2 \times 10^5$ cells/mouse). After 5 weeks, we found that tumors grew quickly in the control group, masses were large, skins upheavals were apparent and skin ulceration appeared. While in the test group, tumors in mice were small, and skin upheaval was almost unobservable. FIG. 11 shows tumor masses excised from the control group (left diagram) and the test group (right diagram).

Although the present invention is described in details in the specific models, those skilled in the art would understand that according to the all teachings as above disclosed, those details can be subjected to various modifications and substitutions, and all these changes fall within the protection scope of the present invention. The whole protection scope of the present invention is given by the appended claims and any equivalents thereof.

What is claimed is:

1. A protein-cell conjugate, which is a conjugate comprising a protein covalently linked to a cell through a linker; wherein:
   the protein is glypican-3;
   the linker is derived from a bifunctional cross-linking agent, and the bifunctional cross-linking agent comprises both a succinimidyl group and a maleimidyl group, wherein the succinimidyl group of the bifunctional cross-linking agent is covalently linked to an amino group of the protein through an amido linkage, and the maleimidyl group of the bifunctional cross-linking agent is covalently linked to a sulfhydryl group on the cell through a thioether linkage; and
   the cell is a lymphocyte.

2. The protein-cell conjugate according to claim 1, wherein the bifunctional cross-linking agent is selected from the group consisting of succinimidyl 4-(N-maleimidomethyl)-cyclohexane-1-carboxylates (SMCC) or an analogue thereof, N-succinimidyl -4-(N-maleimidomethyl)-cyclohexane-1-carboxyl-(6-aminohexanoate), which is a long-chain analogue of SMCC (LC-SMCC), (N-maleimidomethyl)-cyclohexane-1-carboxylic acid-3-sulfosuccinimide ester (SULFO-SMCC), κ-maleimido-undecanoic acid N-succinimidyl ester (KMUA), γ-maleimidobutyric acid N-succinimidyl ester (GMBS), ε-maleimidocaproic acid N-hydroxysuccinimidyl ester (EMCS), meta-maleimidobenzoyl-N-hydroxysuccinimide ester (MBS), N-(α-maleimidoacetoxy)-succinimide ester (AMAS), succinimidyl-6-(β-maleimidopropionylamino) hexanoate (SMPH) and N-succinimidyl 4-(para-maleimidophenyl)-butyrate (SMPB).

* * * * *

UNITED STATES PATENT AND TRADEMARK OFFICE
CERTIFICATE OF CORRECTION

Page 1 of 1

PATENT NO. : 10,071,165 B2
APPLICATION NO. : 14/898209
DATED : September 11, 2018
INVENTOR(S) : Changqing Xia et al.

It is certified that error appears in the above-identified patent and that said Letters Patent is hereby corrected as shown below:

On the Title Page

Item (72) Line 1 to Line 4, the inventor names and locations reading:
- Changqing Xia, Beijing (CN); Yixian Guo, Weifang (CN); Haitao Wu, Beijing (CN); Suigui Wan, Weifang (CN) -

Should be changed to:
- Changqing Xia, Beijing (CN); Haitao Wu, Beijing (CN); Chen Liu, Piscataway, NJ (US); Qunfeng Wu, Wynnewood, PA (US); Yixian Guo, Weifang (CN); Suigui Wan, Weifang (CN) -

Signed and Sealed this
Twentieth Day of October, 2020

Andrei Iancu
*Director of the United States Patent and Trademark Office*